United States Patent
Radmand et al.

(10) Patent No.: US 10,244,982 B2
(45) Date of Patent: Apr. 2, 2019

(54) DETECTION OF HARD AND SOFT TISSUE MASS/DENSITY

(71) Applicant: INVENTIVE MEDICAL DEVICES, LLC, Stratford, CT (US)

(72) Inventors: Reza Radmand, Brookline, MA (US); Ali Moghadam, Trumbull, CT (US)

(73) Assignee: Achaemenid, LLC, Stratford, CT (US)

( * ) Notice: Subject to any disclaimer, the term of this patent is extended or adjusted under 35 U.S.C. 154(b) by 306 days.

(21) Appl. No.: 15/111,177

(22) PCT Filed: Jan. 13, 2015

(86) PCT No.: PCT/US2015/011102
§ 371 (c)(1),
(2) Date: Jul. 12, 2016

(87) PCT Pub. No.: WO2015/108836
PCT Pub. Date: Jul. 23, 2015

(65) Prior Publication Data
US 2016/0331301 A1    Nov. 17, 2016

Related U.S. Application Data

(60) Provisional application No. 61/927,214, filed on Jan. 14, 2014.

(51) Int. Cl.
*A61B 5/00* (2006.01)
*A61B 6/00* (2006.01)
*A61B 5/05* (2006.01)

(52) U.S. Cl.
CPC .......... *A61B 5/4509* (2013.01); *A61B 5/0075* (2013.01); *A61B 5/0088* (2013.01); *A61B 5/0507* (2013.01); *A61B 5/4542* (2013.01); *A61B 5/682* (2013.01); *A61B 5/6835* (2013.01); *A61B 5/4842* (2013.01)

(58) Field of Classification Search
CPC .............................. A61C 19/043; A61C 19/04
See application file for complete search history.

(56) References Cited

U.S. PATENT DOCUMENTS

| 4,564,355 A | 1/1986 | Traiger et al. |
| 5,259,761 A | 11/1993 | Schnettler et al. |

(Continued)

FOREIGN PATENT DOCUMENTS

CA    1259206 A    9/1989

OTHER PUBLICATIONS

EP Search Report and Opinion of EP15737330.9, which is in the same family as International Application No. PCT/US2015/011102, dated Sep. 12, 2017, 7 pages.
M. M. Nazarov, et al., Tooth study by terahertz time-domain spectroscopy, Saratov Fall Meeting 2007: Optical Technologies in Biophysics and Medicine IX, Proc. of SPIE vol. 679.

(Continued)

*Primary Examiner* — Carl H Layno
*Assistant Examiner* — Jon Eric C Morales
(74) *Attorney, Agent, or Firm* — Moyles IP, LLC

(57) ABSTRACT

An apparatus for measuring hard and/or soft tissue abnormalities incidental to dental and/or systemic disease is provided. The apparatus includes a diagnostic device configured for transmitting and receiving non-ionizing electromagnetic waves to measure the patient's hard and/or soft tissue abnormalities associated with the underlying hard and/or soft tissue. The diagnostic device may include at least one of a stent and a diagnostic probe, connected to a computer. The diagnostic device is configured to transmit and receive the electromagnetic waves, and the computer is configured for measure the bone density and/or bone vascular perfusion adjacent and across the patient's hard and/or soft tissue. A method for measuring hard and/or soft tissue abnormalities incidental to dental and/or systemic disease is also provided.

17 Claims, 4 Drawing Sheets

(56) References Cited

U.S. PATENT DOCUMENTS

| | | | |
|---|---|---|---|
| 5,570,182 | A | 10/1996 | Nathel et al. |
| 7,440,788 | B2 | 10/2008 | Jenkins et al. |
| 2004/0122306 | A1 | 6/2004 | Spoonhower et al. |
| 2005/0100866 | A1 | 5/2005 | Arnone et al. |
| 2006/0047190 | A1* | 3/2006 | Jenkins ............... A61B 5/0088 600/340 |
| 2010/0137722 | A1 | 6/2010 | Girkin et al. |
| 2010/0235180 | A1 | 9/2010 | Atkinson |

OTHER PUBLICATIONS

Chinese Search Report and Opinion of CN 201580004469.5 in Chinese, which is in the same family as International Application No. PCT/US15/11102, dated May 31, 2018,11 &14 pages.
Examination Report of EP 15737330.9, which is in the same family as International Application No. PCT/US15/11102, dated Apr. 30, 2018, 7 pages.
International Search Report and Written Opinion of International Application No. PCT/2015/011102, dated May 1, 2015.
I. McCarthy, Application of New Infrared Spectroscopy in the Assessment of Bone Perfusion, Journal of Bone & Joint Surgery, 2012.
M. M. Nazarov, et al., Tooth study by terahertz time-domain spectroscopy, Saratov Fall Meeting 2007: Optical Technologies in Biophysics and Medicine IX.
Carter M. Armstrong, The Truth About Terahertz, Aug. 17, 2012, http://spectrum.ieee.org/aerospace/military/the-truth-about-terahertz.

\* cited by examiner

DETECTION OF HARD AND SOFT TISSUE MASS/DENSITY

CROSS-REFERENCE TO RELATED APPLICATIONS

This application claims priority to PCT Application No. PCT/US2015/011102 filed Jan. 13, 2015, which claims the benefit of U.S. Provisional Application No. 61/927,214 filed Jan. 14, 2014, each of which is incorporated herein by reference in its entirety.

FIELD

An apparatus and method for use in the medical field for detecting bone density and/or diseased hard and soft tissue, particularly changes in bone density resulting from the use of anti-resorptive drugs, is described in which non-ionizing electromagnetic waves are transmitted and received to provide measurements of hard and/or soft tissue abnormalities incidental to dental and/or systemic disease.

BACKGROUND

The hertz (symbol Hz) is a unit of frequency in the International System of Units (SI). It is defined as the number of cycles per second of a periodic phenomenon. The electromagnetic spectrum is the range of all possible frequencies of electromagnetic radiation. The infrared spectrum, (including near infrared, mid-infrared and far infrared), are segments of the electromagnetic spectrum with longer wavelengths than those of visible light, extending from a nominal red edge of the visible spectrum at 700 nanometers (nm) to 1 mm. This range of wavelengths corresponds to a frequency range of approximately 430 Terahertz (THz-$10^{12}$ Hz) down to about 300 GHz (three hundred billion hertz). THz and sub-THz include segments of the electromagnetic spectrum between about far infrared and microwave, which have a wavelength of about 3 mm to about 1 µm, corresponding to frequencies that range from about 100 GHz to 30 THz. These segments of the spectrum cannot be easily gauged with the optical and electronic measurement techniques normally associated with adjacent regions of the spectrum.

It is understood by those skilled in the art that it is possible to use the terahertz segment of the electromagnetic spectrum for diagnosis of dental disease or tissue changes in the hard and soft tissues of an intra and extra oral complexes. For example, use of the electromagnetic spectrum within the terahertz range is well established to diagnose dental decay more accurately and at an earlier stage than other ionizing x-ray techniques. This concept can also be used to illustrate multi-dimensional shapes of such anatomical structures using appropriate hardware and software to convert wave forms into identifiable anatomical images. Typically the waves of this spectrum penetrate the tissue and reflect back to a detector, where they will be read and analyzed. This specific segment of the electromagnetic spectrum will only emit non-ionizing radiation, as compared to other conventional diagnostic tools such as the x-ray or gamma ray that can damage tissue cells.

Advances in technology have made possible the production and detection of infrared radiation with devices that are mobile and operate at room temperature. Perhaps the most commonly used generation method, in medical applications, employs optical rectification, whereby high frequency oscillations of a femtosecond laser pulse are rectified by an optical crystal, leaving only the envelope of the laser signal which is a THz pulse.

What is needed is a device and method that uses an alternative diagnostic means that is mobile, encompasses use of a wide range of the electromagnetic spectrum, has minimal biological adverse effect on the human cells and is practical enough to be used multiple times.

BRIEF DESCRIPTION

According to an aspect, a method and apparatus for detecting and measuring changes in bone perfusion, bone mass and/or density is provided, while in an alternative aspect, a method and device for detecting and measuring diseased tissue is provided. The method and device include using an infrared portion of an electromagnetic spectrum in the detection of bone perfusion and the THZ portion of an electromagnetic spectrum, in detection of bone loss and diseased soft and hard tissue. In a further embodiment, the method and device use the terahertz or infrared waves for detection.

BRIEF DESCRIPTION OF THE FIGURES

A more particular description briefly described above will be rendered by reference to specific embodiments thereof that are illustrated in the appended drawings. Understanding that these drawings depict only typical embodiments and are not therefore to be considered to be limiting of its scope, exemplary embodiments will be described and explained with additional specificity and detail through the use of the accompanying drawings in which:

FIG. 1b is a cross-sectional view of the mandible of FIG. 1a;

Various features, aspects, and advantages of the embodiments will become more apparent from the following detailed description, along with the accompanying figures in which like numerals represent like components throughout the figures and text. The various described features are not necessarily drawn to scale, but are drawn to emphasize specific features relevant to embodiments.

DETAILED DESCRIPTION

Reference will now be made in detail to various embodiments. Each example is provided by way of explanation, and is not meant as a limitation and does not constitute a definition of all possible embodiments.

According to an aspect, a diagnostic device 100 is provided that is configured for transmitting and receiving non-ionizing electromagnetic waves to measure the patient's hard and/or soft tissue abnormalities associated with the underlying hard and/or soft tissue. As described herein, components of one embodiment are intended for use in multiple embodiments, as would be understood by one of ordinary skill in the art. For instance, a computer 30 and/or spectrometer 50 depicted in FIG. 3, is capable of use with a stent 20 of FIGS. 2a and 2b, as will become more apparent with greater discussion hereinbelow.

In an embodiment the waves can be used to identify vascular changes occurring in a jawbone with satisfactory tissue differentiating abilities, as would be found, for instance in dental and/or systemic disease. According to a further aspect, infrared spectroscopy is used as a diagnostic tool for measuring blood perfusion within the jawbone (specifically Near Infrared Spectroscopy—NIRS). In yet another aspect, the terahertz wave is used to detect the soft and hard tissue changes. As used herein, the soft tissue is the tissue that connects, supports, or surrounds other structures and organs of the body, not being bone and includes but is not limited to gums, gingiva, intestinal tissue, vasculature, skin and the like, while the hard tissue includes but is not limited to bone, teeth, and the like.

Figure 1A:
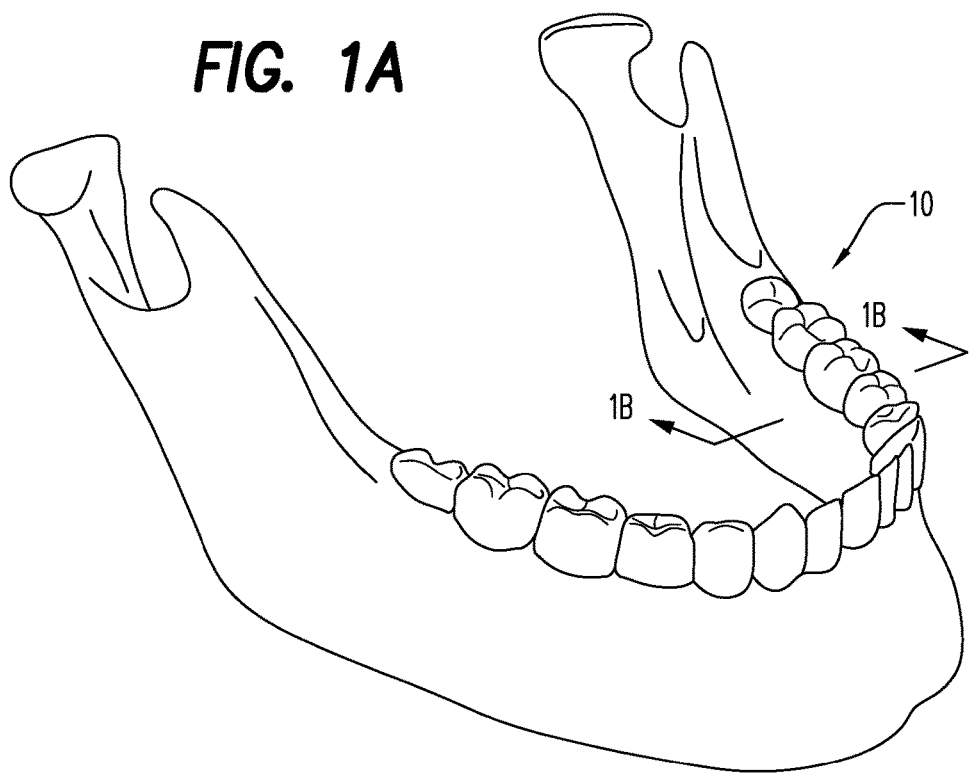
FIG. 1a is a perspective view of a typical mandible (lower jaw) of a patient for which the device and method are adapted according to an embodiment.
Figure 1B:
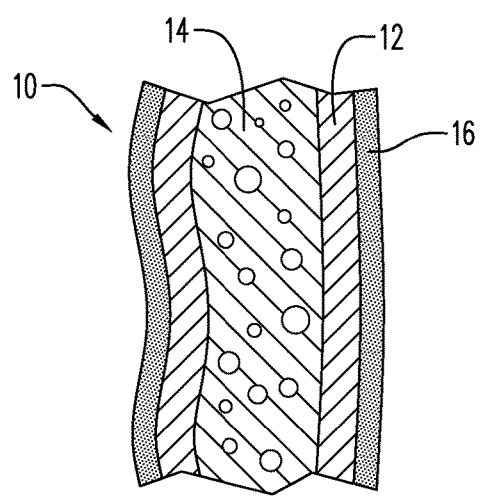

With reference to FIG. 1a, a mandible (a lower jaw or jawbone) 10 of a patient is shown. Although not specifically shown, embodiments described and shown herein that are operational with respect to the mandible are also applicable to the maxilla (upper jaw bone). With reference to FIG. 1b, a cross-sectional view of the mandible of FIG. 1a, the bone 10 includes a cortical bone 12 surrounding spongy bone 14, with the gums and soft tissue 16 covering the bone 10, which comprise hard and/or soft tissue as referenced herein.

Any comparative and relative hypo- or hyper-calcification within the medullary cavity associated with and/or incidental to dental and/or systemic disease, (which contains bone marrow (not shown)), for instance, shows itself as a decrease or increase in its density. Additionally, any reduction in bone perfusion within the medullary bone, may signify hyper calcification or increase in osteoblastic activity of the alveolar bone. A patient on a specific medication regimen that may change the density of the bone within short time intervals may need to be followed up closely as these changes occur. The use of electromagnetic radiation (i.e., THZ Time Domain, Infrared Fourier Transform), is particularly beneficial to patients who are receiving medications for osteoporosis or metastatic bone disease secondary to multiple myeloma, breast or prostate cancer, to name a few. The use of anti-resorptive medications is necessary to mitigate the loss of bone mass, leading to pathologic fracture of the bone.

In an embodiment, it is important to repetitiously and accurately measure the changes occurring in the bone for at least the following reasons: 1) gage the efficacy of these anti-resorptive drugs; 2) accurately follow and measure, in short time intervals, the incremental changes that occur in the jawbone during the administration of the anti-resorptive therapy, which according to current technology capabilities is not practical (the only current methods for bone density evaluation are ionizing radiation or MRI); 3) to develop an alternative protocol for drug administration, based on the changes that occur in the jawbone, hence reducing the incidence of osteonecrosis of the jaw (ONJ); 4) to detect the excessive and sometimes irreversible damage to the vital components of the bone complex (for example in the jawbone, this condition could lead to ONJ), with the aim to reduce or stop the use of these medications, in time, when such changes are detected; and 5) to evaluate the healing progression within the alveolar bone, post ONJ.

As discussed above, the full electromagnetic spectrum can be used to measure bone density/mass and bone vascular perfusion, as described herein. Since the infrared wave has a low tissue absorption rate, it is capable of penetrating through soft and hard tissue, up to several centimeters. The infrared wave is mainly absorbed by hemoglobin molecules, which aid in obtaining a value for the amount of vascular perfusion within the bone being measured. By measuring the vascular abundance in, for instance, the alveolar bone, a degree of osteoblastic activity, (bone deposition), during the administration of anti-resorptive therapy drugs or bisphosphonate medicines such as XGEVA® (denosumab) manufactured by Amgen Inc., to patients with metastatic bone disease (such as Giant Cell Tumor of Bone) and osteoporosis. Although these drugs are administered to countermand bone loss and generate tissue healing, in rare instances, death of bone cells and/or tissue result. Approximately 4-5% of patients taking such drugs experience a serious side effect of ONJ, also known as avascular necrosis of the jaw, resulting in drastic and unpleasant symptoms, including pain, inflammation of the surrounding soft tissue, secondary infection and/or drainage. The definitive sign of ONJ is the exposure of mandibular or maxillary bone through the gingiva over 8 weeks in duration. There may be no symptoms for weeks or months, until lesions with exposed bone appear. Use of the infrared wave and associated detection equipment as discussed in greater detail below for early detection and to measure the progressive diminishing of the alveolar vasculature can greatly benefit patients suffering from this debilitating disease.

Currently, as previously mentioned, the only way to closely monitor such changes is with the use of ionizing radiation and expensive MRI techniques.

According to an aspect, an apparatus and method for measuring hard and/or soft tissue abnormalities incidental to dental and/or systemic disease is provided. In an embodiment, and with reference for instance to FIGS. 2a and 2b, a stent 20 is selected to overlay a patient's hard and/or soft tissue (see, for instance, FIG. 1). According to an aspect, the stent 20 is selected based on the relative size of the mouth of the patient. According to an aspect, the stent 20 is customizable, that is, the stent 20 is created from impressions of each individual patient's mouth, and sized to overlay each patient's hard and/or soft tissue. As would be understood by one of ordinary skill in the art, depending on the particular circumstances of each individual patient, the lower and/or upper jaw may be limited in number of teeth 18 (including having no teeth), may have bone loss, and the like, when the stent 20 is customized.

Figure 2A:
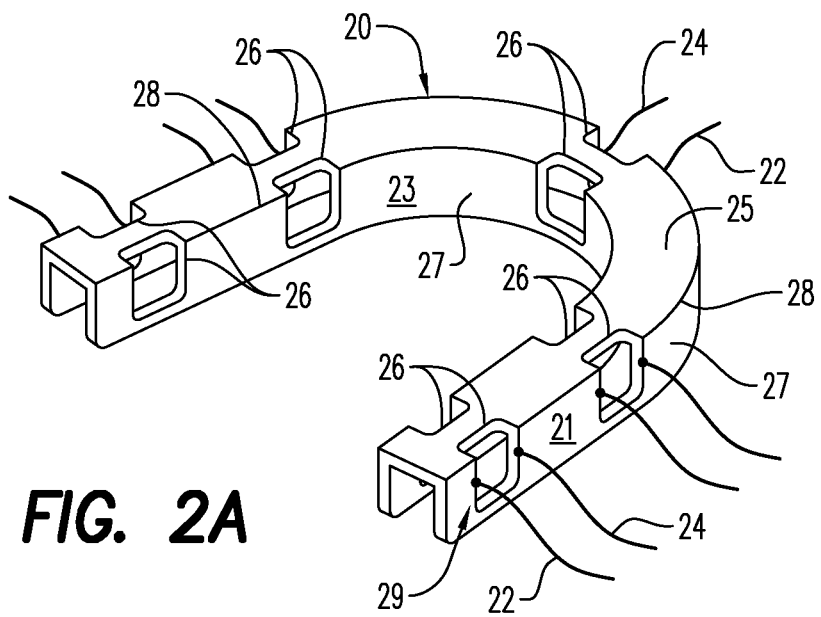
FIG. 2a is a perspective view of a stent according to an embodiment.
Figure 2B:
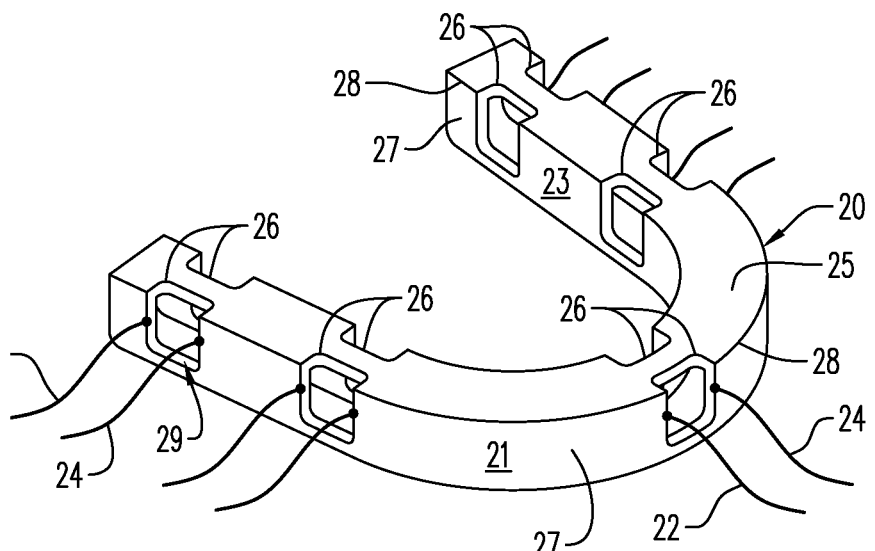
FIG. 2b is a perspective view of a stent according to an embodiment.
Figure 3:
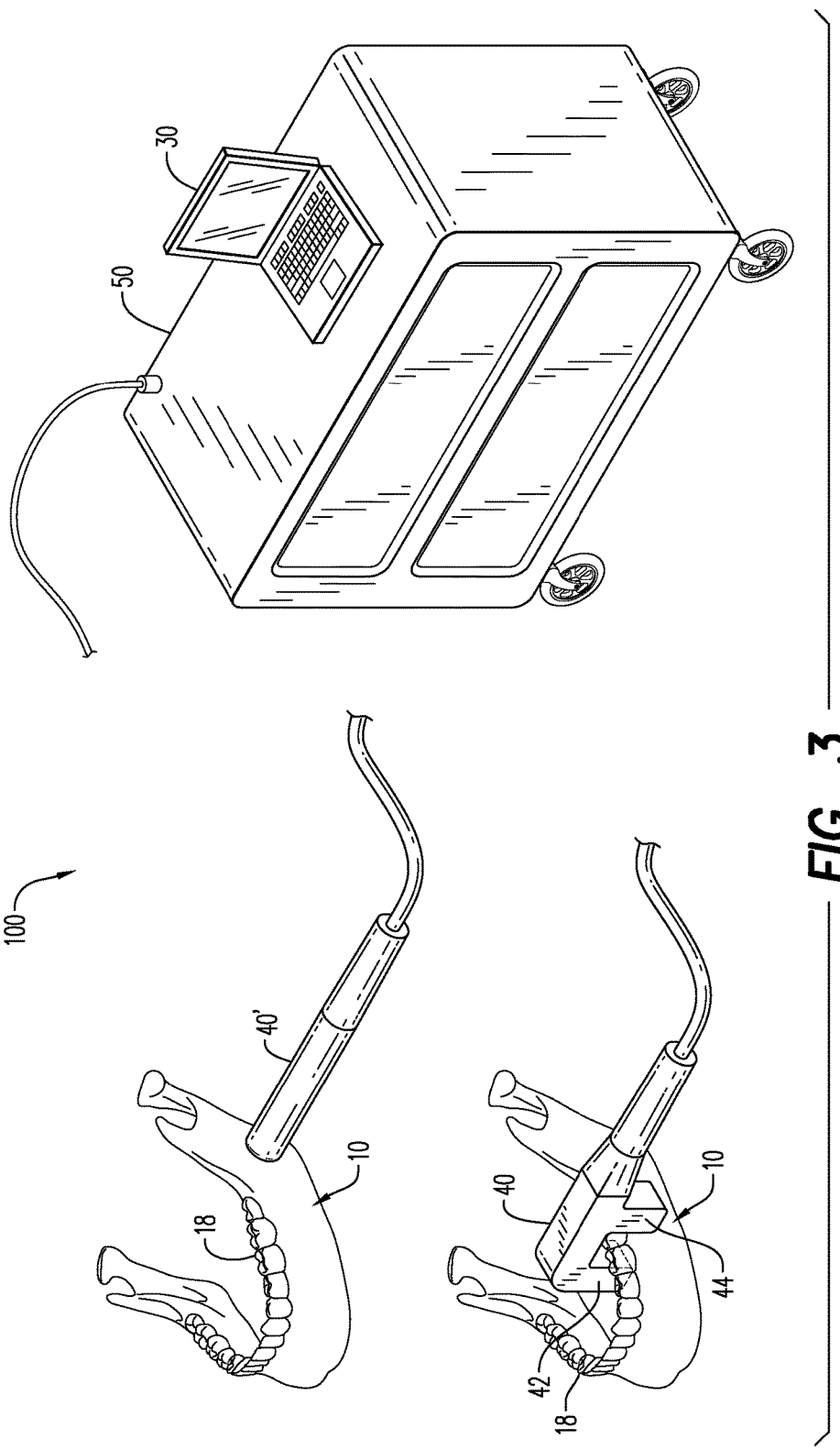
FIG. 3 is a perspective view of bone density measuring device according to an embodiment.

With reference to FIGS. 2a and 2b, such an oral stent 20 is provided. In an embodiment, the overall dimensions and shape of the stent 20 may be formed through conventional dental molding techniques and are designed to fit over the teeth 18 (see FIG. 3) or edentulous jaw of the patient and lay in proximity to the gums 16 of the patient. In an embodiment, the stent 20 has a plurality of detection ports or openings 26, which are strategically positioned along the stent 20 and selected for positioning adjacent segments of the jawbone 10 having different bone density. As an example, an anterior portion of bone of the lower jaw 10 (FIG. 1) may have a lower bone density than a posterior portion or segment of the bone, and is hence considered more vascular. The stent 20 typically includes an upper surface 25, flanked by sides 27 of the stent 20, along an edge 28.

In an embodiment, a pair of the plurality of detection ports 26 comprises a buccal-side 21 detection port 26 and a lingual-side 23 detection port 26. In an embodiment, the lingual-side detection port is positioned opposite the buccal-side detection port. In a further embodiment, the buccal-side detection port is configured as a mirror image of the lingual-side detection port. According to an aspect, the buccal-side detection port is configured to transmit the electromagnetic wave, while the lingual-side detection port is configured to receive data associated with the transmitted/received wave, and return data to an attached computer 30, which is configured for calculating, from the received data, the bone density and/or bone vascular perfusion adjacent and across each of the pairs of the plurality of ports 26. According to an aspect, the pairs of detection ports 26 are positioned along an edge 28 of the stent 20.

In an embodiment, the buccal side 21 of the stent 20 includes wires 22/24 connected to outer edges of each buccal-side port 26 as shown in FIGS. 2a and 2b for initiation of transmission of the electromagnetic wave and for receiving data related to measured bone density. In an embodiment, a wire in 22 is connected to a posterior edge of port 26, which is positioned on the buccal side 21 of the stent 20, while a wire out 24 is connected to an anterior edge of the same port 26. Positioned on the stent 20 opposite to the wires 22, 24, the port(s) 26 positioned on the lingual side 23 may include, for instance, a detector or sensor for receiving the transmitted wave (not shown). The plurality of ports 26 are capable of transmitting the sensed or measured IR wave related to the bone density and feeding the data back to a computer for analysis (as discussed with greater detail with reference to FIG. 3 hereinbelow).

In an embodiment, the wires 22, 24 are connected to a computer 30 and/or a spectrometer (see FIG. 3) or alternatively, a wireless connection may be made, which initiates a wave having a length and/or frequency in the electromagnetic spectrum described herein that ranges from the infrared range to the THZ range (approximate frequency range of 1011-1014 Hz) and transmits the wave from, for instance, the buccal side of the stent 20 through the bone across the port 26, and detects the wave to create an image of the bone density. The wires 22/24 are thus configured for transmitting the electromagnetic waves and receiving data associated therewith. According to an aspect, the wires 22/24 are attached at a first end 29 of the wires 22/24 to the buccal side ports 26, and attached at a second end to the computer 30 (not shown). In an embodiment, the diagnostic device is configured to transmit the electromagnetic waves from the buccal-side detection ports 26, through the patient's bone, and the lingual-side detection ports 26 being configured to receive the electromagnetic waves, such that changes occurring in the bone density and/or bone vascular perfusion are repetitiously and accurately measured, wherein the electromagnetic waves being infrared or terahertz electromagnetic waves In an embodiment, use of a portable THZ or IR (Infrared) device will allow a flat surface or a double surface probe 40 to be placed on the skin or gum tissue, over the lower or upper jaw bone, through a stent 20 that fits securely, repetitiously and consistently over the upper or lower jaw.

In an alternative embodiment and as seen in FIG. 3, the electromagnetic waves are transmitted/detected to/from a diagnostic probe 40, 40' from a spectrometer 50, configured to measure electromagnetic waves having a frequency of between about 100 GHz to about 430 THz, or any portions or segments thereof. As shown herein, a flat surface diagnostic probe 40' can be placed in proximity to the jawbone 10, and/or a double or multiple surface diagnostic probe 40 having a plurality or arms. As shown in FIG. 3, the probe 40 has a first arm 42 and a second arm 44, which can be placed in proximity to the teeth 18 or bone 10, such that the first arm 42 of the probe 40 extends along a lingual surface of the teeth 18 or bone 10, while an opposite arm or second arm 44 extends along a buccal surface of the teeth 18 or bone 10. In other words, the plurality of arms 42, 44 of the probe 40 straddle opposing sides of the teeth 18 of bone 10. The computer 30 is configured to receive the electromagnetic "fingerprint" spectra waves transmitted through the bone and to detect minute changes in the density of the bone, over the course of treatment using the anti-resorptive therapeutics.

Although not shown, it is further contemplated herein that the probe 40, 40' could be used in conjunction with a stent 20. In such an embodiment, and as would be understood by one of ordinary skill in the art, the stent 20, which in an embodiment, has been customized for the particular, individual patient, would be used by the practitioner for locating the individual areas of the jaw to be measured.

It is well understood by those of ordinary skill in the art that the use of ionizing radiation is cumulative and harmful when used numerous times over a long period of time. Hence, according to an aspect, the patient may benefit from an alternate technique, which uses non-ionizing electromagnetic waves that can be used multiple times without the harmful side effects of the ionizing radiation such as X-rays and gamma rays. The shorter wavelengths of the infrared band will result in more clear spatial resolution and are therefore more accurate for diagnosis and identification of these subtle tissue changes. There have been many in vitro experiments in dentistry to determine the characteristics of enamel and dentin in detecting changes that can occur in these tissues in early dental caries.

In soft tissue studies, THz radiation was able to differentiate between the normal versus the diseased tissue even when compared with a conventional in vitro histological test. The objective according to an embodiment is to diagnose the extent of the diseased tissue (cancer of the oral soft tissue or skin) and in the process, conservatively remove as little of the surrounding healthy tissue as possible. An abnormal oral tissue (tongue, gum, inside of the cheek) to the naked eye or touch, can be evaluated first with the use of infrared radiation, which can distinguish quite accurately between normal tissue and abnormal or cancerous tissue. In an embodiment, the invasive nature of diseased tissue can also be detected, in an effort to establish a more conservative yet accurate approach to its treatment.

Figure 4:
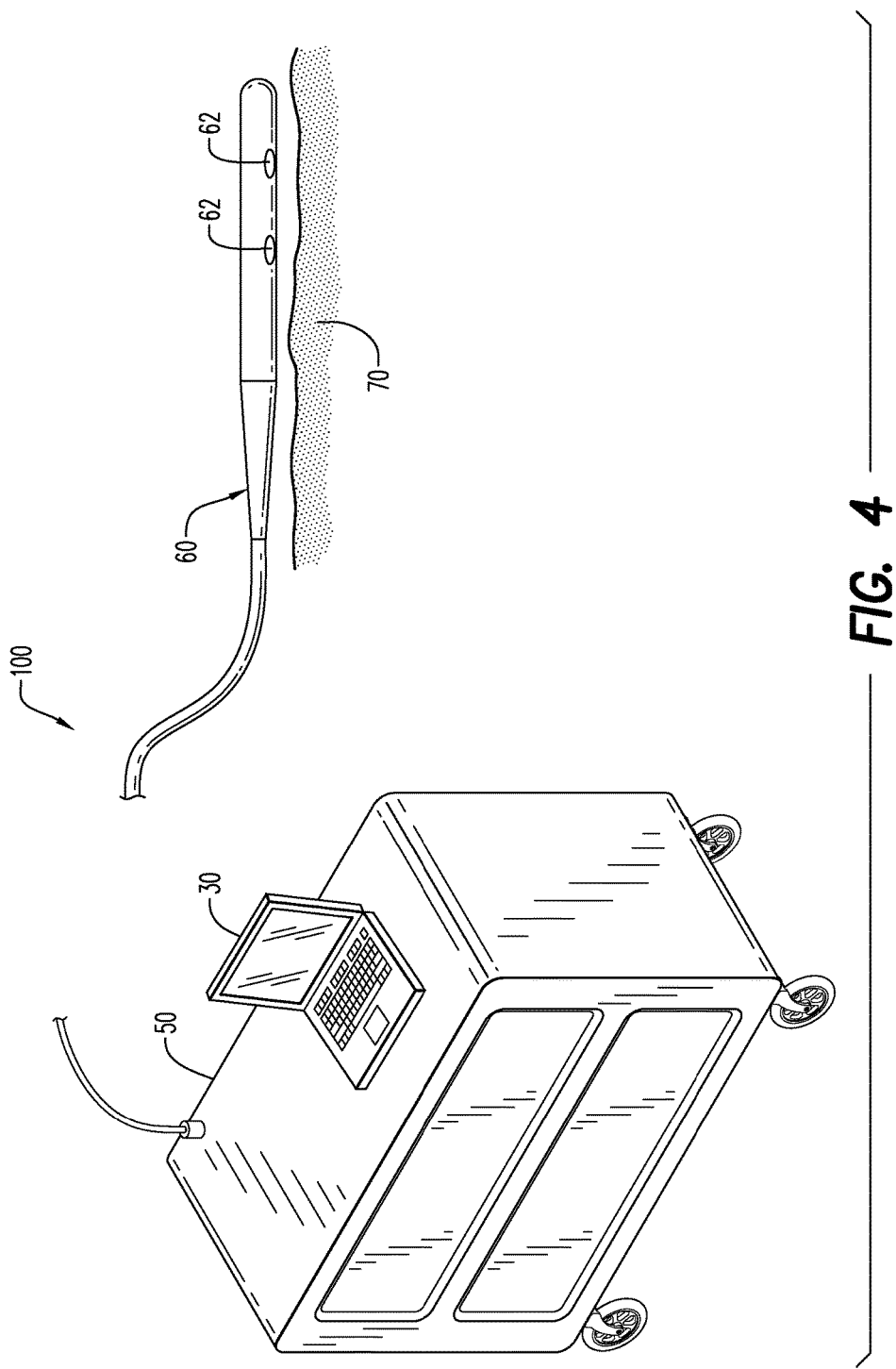
FIG. 4 is a perspective view of an alternative bone density measuring and diseased tissue detection device according to an embodiment.

Similarly, according to an aspect, this technology can be used to view the internal tissue integrity such as tonsillar, genitourinary and the upper or lower gastrointestinal passages. In this alternative embodiment as shown in FIG. 4, the THz spectrometer 50 transmits/receives waves through an endoscopic probe 60 to detect unhealthy tissue 70 endoscopically. In this embodiment, the flexible endoscopic device with THz probe arrangement 60 is used, and the internal tissue 70 surfaces are scanned with the use of the THz radiation and fed back to the spectrometer machine 50 for analysis and diagnosis in a 3D format. In an embodiment, the endoscopic probe 60 has a plurality of transducers 62 arranged along the surface of the probe 60 for transmitting and detecting the infrared waves to detect tissue abnormalities.

According to an aspect, computerized diagnostic three-dimensional illustrative models can be generated, which can be used to plan for surgical procedures. Examples whereby such models would be beneficial include those in the field of craniofacial surgery in congenitally deformed patients, orthognathic surgery (surgery to correct conditions of the jaw and face related to structure, growth, sleep apnea, TMJ disorders, malocclusion problems owing to skeletal disharmonies, or other orthodontic problems that cannot be easily treated with braces) or dental implant placement in the jawbone. Additionally, in head and neck cancer therapy, for example, prior to elimination of the diseased tissues, it is essential to delineate the extent of pathology in the affected area. Subsequent surgery and/or ionizing radiation therapy to the region is then necessary to treat the disease. THz radiation can be instrumental in planning a conservative mapping of the diseased area in an attempt to identify the extent of pathology and minimize damage to the healthy surrounding tissue. In a further embodiment, the computer is configured to evaluate progression of tissue healing, secondary to ONJ.

The components and methods illustrated are not limited to the specific embodiments described herein, but rather, features illustrated or described as part of one embodiment can be used on or in conjunction with other embodiments to yield yet a further embodiment. It is intended that the embodiments include such modifications and variations. Further, steps described in the method may be utilized independently and separately from other steps described herein.

While the embodiments have been described with reference to a preferred embodiment, it will be understood by those skilled in the art that various changes may be made and equivalents may be substituted for elements thereof without departing from the scope. In addition, many modifications may be made to adapt a particular situation or material to the teachings without departing from the essential scope thereof.

In this specification and the claims that follow, reference will be made to a number of terms that have the following meanings. The singular forms "a," "an" and "the" include plural referents unless the context clearly dictates otherwise. Furthermore, references to "an embodiment" are not intended to be interpreted as excluding the existence of additional embodiments that also incorporate the recited features.

Advances in science and technology may make equivalents and substitutions possible that are not now contemplated by reason of the imprecision of language; these variations should be covered by the appended claims. This written description uses examples to disclose the various embodiments, including the best mode, and also to enable any person of ordinary skill in the art to practice the embodiments, including making and using any devices or systems and performing any incorporated methods. The patentable scope is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for measuring hard and/or soft tissue abnormalities incidental to dental and/or systemic disease, comprising:
    a stent selected to overlay a patient's hard and/or soft tissue, wherein the stent comprises a plurality of detection ports positioned along the stent, the plurality of ports being selected for positioning adjacent differing density found in the hard and/or soft tissue of the patient; and
    a diagnostic device configured for transmitting and receiving non-ionizing electromagnetic waves to measure the patient's hard and/or soft tissue abnormalities associated with the underlying hard and/or soft tissue adjacent the plurality of detection ports, wherein
    the diagnostic device comprises wires connected to at least a portion of the plurality of ports at a first end and the wires being connected to a computer at a second end, the wires being configured for transmitting the electromagnetic waves and receiving data associated therewith, and the computer configured for calculating, from the received data, the bone density and/or bone vascular perfusion adjacent and across each of the plurality of ports,
    the computer is configured to produce three-dimensional images for mapping surgical procedures, and
    at least a pair of the plurality of detection ports comprising a buccal-side detection port and a lingual-side detection port, the lingual-side detection port being positioned opposite the buccal-side detection port, the pairs of detection ports being positioned along an edge of the stent.

2. The apparatus of claim 1, wherein the stent being customizable and sized to overlay each patient's hard and/or soft tissue.

3. The apparatus of claim 1, wherein the buccal-side detection ports being a mirror image of the lingual-side detection ports.

4. The apparatus of claim 1, wherein the buccal-side detection ports being configured to transmit the electromagnetic waves through the patient's bone and the lingual-side detection ports being configured to receive the electromagnetic waves, such that changes occurring in the bone density and/or bone vascular perfusion are repetitiously and accurately measured, wherein the electromagnetic waves being infrared or terahertz electromagnetic waves.

5. The apparatus of claim 4, wherein the stent being customizable and sized to overlay each patient's hard and/or soft tissue.

6. The apparatus of claim 5, wherein the computer is configured to evaluate progression of tissue healing, secondary to ONJ.

7. An apparatus for measuring hard and/or soft tissue abnormalities incidental to dental and/or systemic disease, comprising:
    a stent selected to overlay a patient's hard and/or soft tissue, wherein the stent comprises a plurality of detection ports positioned along the stent, the plurality of ports being selected for positioning adjacent differing density found in the hard and/or soft tissue of the patient and wherein a pair of the plurality of detection ports comprising a buccal-side detection port and a lingual-side detection port positioned opposite the buccal-side detection port;
    a diagnostic device configured for transmitting and receiving non-ionizing electromagnetic waves to measure the patient's hard and/or soft tissue abnormalities associated with the underlying hard and/or soft tissue adjacent the plurality of detection ports;
    a diagnostic probe, the diagnostic probe being configured to transmit and receive the electromagnetic waves when positioned adjacent the pair of the plurality of detection ports; and
    a computer connected to the diagnostic probe, the computer being configured for calculating the bone density and/or bone vascular perfusion adjacent and across each of the pair of the plurality of detection ports.

8. The apparatus of claim 7, wherein the stent being customizable and sized to overlay each patient's hard and/or soft tissue.

9. The apparatus of claim 7, wherein the computer is configured to produce three-dimensional images for mapping surgical procedures.

10. The apparatus of claim 7, wherein at least a pair of the plurality of detection ports comprising a buccal-side detection port and a lingual-side detection port, the lingual-side detection port being positioned opposite the buccal-side detection port, the pairs of detection ports being positioned along an edge of the stent.

11. The apparatus of claim 10, wherein the stent being customizable and sized to overlay each patient's hard and/or soft tissue.

12. The apparatus of claim 11, wherein the computer is configured to evaluate progression of tissue healing, secondary to ONJ.

13. An apparatus for measuring hard and/or soft tissue abnormalities incidental to dental and/or systemic disease, comprising:
a diagnostic device configured for transmitting and receiving non-ionizing electromagnetic waves to measure the patient's hard and/or soft tissue abnormalities associated with the underlying hard and/or soft tissue, the diagnostic device comprising a diagnostic probe and a computer, the diagnostic probe being configured to transmit and receive the electromagnetic waves, the diagnostic probe being connected to the computer, the computer being configured for measuring the bone density and/or bone vascular perfusion adjacent and across the patient's hard and/or soft tissue.

14. The apparatus of claim 13, wherein the probe comprises a single, flat surface.

15. The apparatus of claim 13, wherein the probe comprises a plurality of surfaces, the plurality of surfaces configured to straddle the patient's hard and/or soft tissue.

16. The apparatus of claim 13, wherein the probe being configured for use in diagnosing the patient's soft tissue, the soft tissue being an internal body cavity soft tissue.

17. The apparatus of claim 13, wherein the computer is configured to evaluate progression of tissue healing, secondary to ONJ.

* * * * *